United States Patent [19]

Ridge

[11] Patent Number: 4,794,631
[45] Date of Patent: Dec. 27, 1988

[54] CARDIOVASCULAR PHANTOM

[75] Inventor: William B. Ridge, Sunnymead, Calif.

[73] Assignee: Vari-X, Inc., Irvine, Calif.

[21] Appl. No.: 915,819

[22] Filed: Oct. 6, 1986

[51] Int. Cl.[4] .............................................. G01D 18/00
[52] U.S. Cl. ..................................... 378/207; 378/18; 378/99
[58] Field of Search ................... 378/207, 99, 164, 18; 250/252.1; 29/831, 841

[56] References Cited

U.S. PATENT DOCUMENTS

| | | | |
|---|---|---|---|
| 3,770,956 | 11/1973 | Johnson | 378/164 |
| 4,432,014 | 2/1984 | Roos et al. | 378/99 |
| 4,586,436 | 5/1986 | Denny et al. | 102/206 |
| 4,649,561 | 3/1987 | Arnold | 378/207 |

OTHER PUBLICATIONS

*Reference Data for Radio Engineers*, fourth edition, IT&T Co., New York, 1957, pp. 107–110.

Primary Examiner—Craig E. Church
Assistant Examiner—T. N. Grigsby
Attorney, Agent, or Firm—George F. Bethel; Patience K. Bethel

[57] ABSTRACT

This specification sets forth a cardiovascular phantom. The phantom is adapted for placement on a table between an X-Ray tube and a film camera. The phantom is formed from absorptive material comprising at least one layer of metallic material on a plastic board. The metallic material is formed in the shape of arterial vessels from a radiopaque material. The radiopaque material and phantom absorb the X-Rays in an analogous manner to a person's heart. The phantom provides an analog to allow adjustments for the X-Ray process used for cardiovascular analysis.

22 Claims, 3 Drawing Sheets

CARDIOVASCULAR PHANTOM

BACKGROUND OF THE INVENTION

1. Field of the Invention

The field of this invention is within X-Ray photography. More particularly, it has to do with cine X-Ray photography with respect to anatomical coronary evaluation. It particularly deals with establishing cine photographic images on a correct basis and the adjustment of the equipment for cine X-Ray analysis and evaluation of coronary vessels and surrounding tissue.

2. The Prior Art

Cardiovascular or anatomical coronary vessel phantoms have been used in the past for providing adjustment and analysis of X-Ray equipment. In particular, the X-Ray equipment is of the type used for cine filming of heart vessels and related tissue and vessels.

It has been known to utilize cine film for photographing heart vessels on a dynamic basis. This is due to the fact the heart vessels in particular are in a dynamic state inasmuch as the heart is constantly pumping and can be evaluated more favorably by cine techniques rather than still X-Rays.

During the evaluation of heart vessels, the cine film is run at approximately thirty frames per second after a dye has been injected into the heart vessels. The dye is usually of an iodine type which is absorptive of X-Rays. The X-Ray absorption allows a pattern or a reproduction of a film to evince the various aspects of the heart vessels so as to determine clogged arteries and other characteristics of a given heart.

In the past, it has been known to utilize an anatomical coronary vessel phantom in the form of a pig's heart. The pig's heart was encapsulated within plastic and crafted to provide an anatomical equivalent to a human heart. The vessels were provided with a radiopaque material for radiographic modelling to provide setup adjustments for cine equipment.

The radiation absorption characteristics of the block and the pig's heart with the radiopaque material therein was used to adjust cine equipment for accurate filming.

The organic characteristics of a pig's heart, absorptive characteristics of the radiopaque material in the vessels of the pig's heart and other aspects of the anatomical coronary vessel phantoms of the prior art could not be consistently established. As a consequence, certain spurious images were evinced in the use of such phantoms. Also, scatter was encountered, as well as other aspects so that the sharpest available image for cine film could not be maintained.

This particular invention utilizes a consistently absorptive structure for adjusting and maintaining cine equipment for cardiovascular analysis. The adjustment can readily take place in an easy and facile manner. The phantom of this invention is consistent with regard to absorptive characteristics, the angles that it provides, the general degree of scatter and the overall impression with regard to tissue equivalents. In this manner, cine equipment is adjusted to provide substantially optimal results to the viewer of cardiovascular films.

SUMMARY OF THE INVENTION

In summation, this invention comprises a cardiovascular phantom having printed circuitboards with X-Ray absorptive material thereon in a sandwich configuration to effectuate accurate cine film reproductions.

More particularly, it incorporates a cardiovascular phantom or anatomical coronary vessel phantom wiht a plurality of circuitboards which have X-Ray absorptive material such as lead thereon. The lead is provided on circuitboards which are sandwiched together in overlying relationship. The adjacent area to the lead vessels on the circuitboards is provided with anatomically correct tissue equivalents so that reproduction of the coronary arteries, as well as the myocardium diaphragm and the lung field are substantially in the realm of human characteristics.

The provision of the foregoing for cine analysis is provided consistently by the foregoing configuration. The foregoing configuration thereby allows a consistent adjustment of cine equipment so that the equipment can be adjusted with respect to those characteristics of the human anatomy that it intends to view on a sharp and consistent basis. The sharp and consistent basis thereby provides for proper cine filming by having optically adjusted cine equipment based upon consistent feedback through a consistently designed phantom analogous to the human body.

DESCRIPTION OF THE PREFERRED EMBODIMENTS

Figure 1:
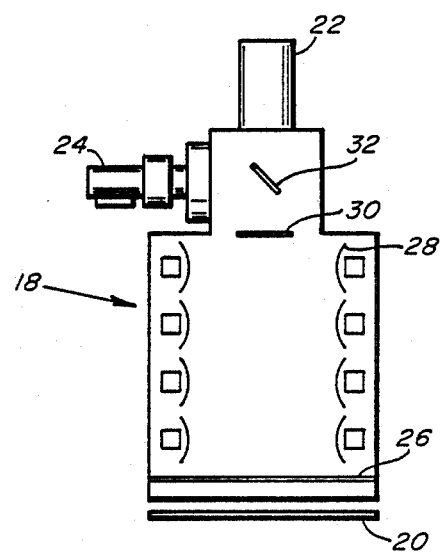
FIG. 1 shows a schematic presentation of the utilization of a cardiovascular phantom of this invention in conjunction with X-Ray tubes and cine recording equipment.
Figure 1:
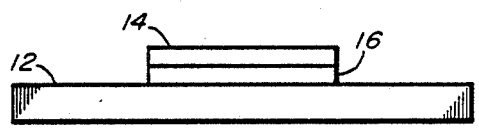
Figure 1:
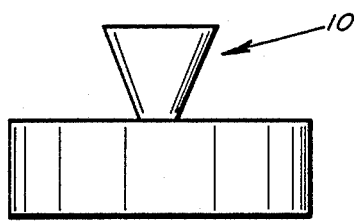

Looking more particularly at FIG. 1, it can be seen wherein an X-Ray tube 10 is shown that emits X-Rays from a general point source. The X-Ray tube 10 underlies a table 12 which is utilized for holding a patient or the subject. The table 12 generally has a patient attenuator 14 thereover. Underlying the patient attenuator is the cardiovascular phantom 16 of this invention which shall be detailed hereinafter.

In order to provide for X-Ray photography, or cine recordation, as well as viewing of the subject, an image intensifier 18 is utilized. The image intensifier overlies a grid 20. The grid 20 has a plurality of narrowly placed strips in order to attenuate scattered X-Rays. As can be appreciated, when X-Rays are scattered off of a subject such as a body, they are received in an unusable form or are not such wherein they provide a sharp image. To limit the scatter, the grid is utilized which serves to attenuate and provide substantially only those X-Rays passing through the subject matter directly from the X-Ray tube.

On top of the image intensifier is a TV camera 22 which can be used dynamically to view the subject such as the heart that is under study. On the side of the image intensifier is a film camera which provides a cine film recordation.

The image intensifier incorporates a phosphorous screen 26 and a series of focussing coils 28 which tend to cause the X-Ray beams to be directed toward a phosphorous output lens 30. The beam from the lens 30 is split by a beam splitter 32 to provide the output to the TV camera and the film camera, respectively numbered 22 and 24.

In order to adjust the film camera 24 and provide for accurate cine recordation by appropriate adjustment, the cardiovascular phantom 16 is implaced on the table 12 rather than the patient. The cardiovascular phantom helps to provide for aperture adjustment of the cine camera. It also provides focussing of the cine camera. As also can be understood, the amount of X-Ray dose for the provision of a proper image to the cine camera must be adjusted. This also is enhanced as to its adjustment, by the cardiovascular phantom 16 providing a consistent absorptive material.

It should be kept in mind that the phantom 16 provides an equivalent result as to absorptive characteristics on film. In other words, the characteristics of the phantom are the analog of a body as it is recorded on film. It is not equivalent to the absorptive characteristics of a body due to the aspects of scatter and other relevant characteristics. In effect, the phantom does not absorb all the X-Rays but allows for an equivalent absorption as to the way it would be on film in an analogous manner to the way a body would absorb the X-Rays that are provided to the image intensifier and concomitantly the film.

Figure 2:
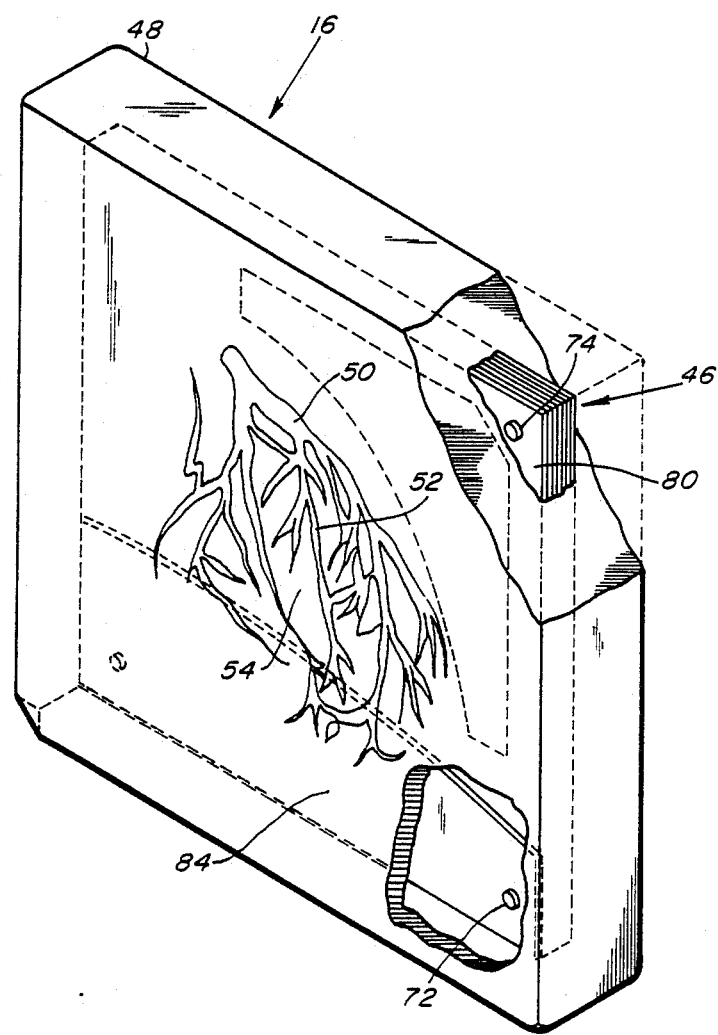
FIG. 2 shows a broken away perspective view of the cardiovascular phantom of this invention.

Looking more particularly at FIG. 2, it can be seen that the cardiovascular phantom 16 is shown in a perspective broken away view. The cardiovascular phantom 16 is provided with a total of six circuitboards, each having an outline in lead of the heart vessels. A copper plate which shall be described hereinafter and a minor copper plate overlying the six foregoing circuitboards are provided to create the absorptive characteristics of the heart and the diaphragm.

Looking more particularly at the phantom, it can be seen wherein the sandwich of circuitboards and plates 46 are shown with the edges thereof exposed. The foregoing are encapsulated within an acrylic block 48 or can be potted in any other suitable manner. The arborescent outline of the heart vessels is shown on the face thereof. The arborescent outline of the heart vessels is such wherein only the arterial vessels are shown. This can be seen in the form of major heart vessels 50 and the minor heart vessels 52. Interiorly of the major and minor heart vessels is a space 54 for providing a film analysis by means of a densitometer which will be expanded upon hereinafter.

Figure 3:
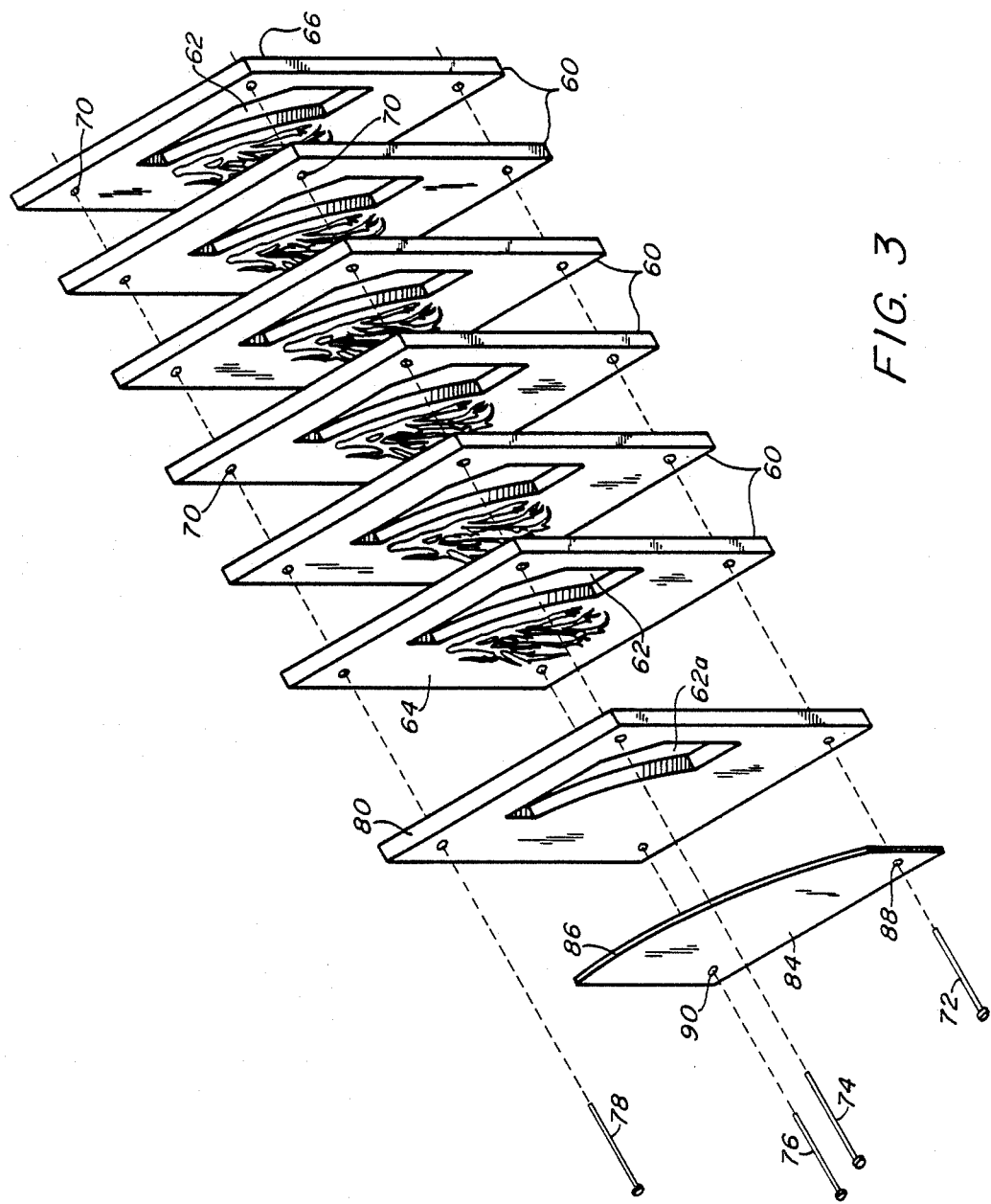
FIG. 3 shows a perspective exploded view of the attentuating and body absorptive materials that comprise the cardiovascular phantom of this invention.

The sandwiched plates and boards which have been generally shown as plates 46, are shown in greater detail in FIG. 3. In particular, a plurality of six circuitboards 60 are shown having a space 62 in each one. Each one of the cicuitboards 60 are identical as to the material printed thereon.

In particular, the six circuitboards are made of any type of suitable circuitboard material such as plastic, or reinforced plastic having a lead coating. The lead coating is etched away to provide the arborescent appearance of the system of major arteries 50 and 52 on the faces of the boards. In particular, the arborescent appearance of the system of arteries 50 and 52 is provided identically on faces 64 and back faces 66 on the other side which are not shown in the perspective view.

The arterial showing is such wherein the lead of the circuitboards is etched away to provide the arterial appearance on each side. In this manner, when the boards 60 are in overlying relationship and indexed accurately, the images of the arteries shown generally in FIG. 2 are such wherein there are twelve (two on each board) in overlying relationship. One arterial area with its lead surface overlies another arterial area behind it on the same board so that a consistent image is provided from one side to the other when the boards are sandwiched together.

The arborescent outline trace of the system of arterial vessels 50 and 52 on the two portions 64 and 66 on each side of panel 60 when in overlying indexed relationship provide approximately thirty six thousandths of an inch of lead in total. This is due to the fact that each circuitboard lead outline of the arterial vessels thereon is about three thousandths of an inch thick. Thus, the total sandwich of the arterial vessels as outlined on the boards 60 provide for the thirty six thousandths of an inch of lead in absorptive overlying relationship analogous to the arterial vessels. This is equivalent to the amount of absorptive characteristics of dye when placed in the vessels of a human subject.

Iodine is usually the absorptive dye that is utilized. It absorbs X-Rays that are low energy X-Rays. The overlying lead vessel outline of three thousandths of an inch on each circuitboard combining for thirty six thousandths of an inch lead surfacing is the equivalent in the absorptive characteristics of dye in the heart vessels when the film is exposed in the cine camera 24. Thus, an analogous display can be provided by this phantom to that of the iodine absorptive characteristics in a vessel.

Again, looking more particularly at FIG. 3, it can be seen where the circuitboards 60 are provided with holes or openings 70. These holes or openings 70 are indexed over each other to allow for screws 72, 74, 76 and 78 to be implaced within the holes 70 of the boards for holding the boards 60 in overlying indexed relationship. The screws can be plastic screws with a plastic nut that secures them together or any other form of fastening means.

In order to allow for an analog to the lung field, spaces 62 are cut out of each board. The spaces 62 allow for the lung field which is relatively porous in absorptive characteristics to be imaged correctly on the cine film. The heart itself as to the absorptive characteristics of the tissue thereof is provided by a copper plate 80. The upper area of plate 80 has an opening 62a analogous to the prior openings for purposes of creating the lung field. The copper plate 80 is relatively absorptive and can be substituted by other metals as will be described hereinafter.

A diaphragm plate 84, is shown having a curved surface 86 thereto. The diaphragm plate 84 is also made of copper and is indexed into place through openings 88 and 90 passing therethrough. Thus, in combination, the plates 80 and 84 when combined together allow for absorptive characteristics of the diaphragm and the heart.

The copper of the plates 80 and 84 can be substituted by other metals such as aluminum, beryllium, lead and brass. Furthermore, other X-Ray absorptive materials can be utilized. However, it must be understood that the thickness or thinness of the foregoing materials vary in order to provide analogous absorptive characteristics of the heart by copper plate 80 and the diaphragm by copper plate 84.

The cardiovascular phantom 16 has been designed to provide an anatomically correct tissue equivalent reproduction of the coronary arteries which are the lead artery outlines 50 and 52. The myocardium diaphragm equivalent is provided by plate 84 when combined with plate 80 and the heart tissue by plate 80. The lung field is provided by the pass through spaces 62 in cooperation with the acrylic potting material 48 that is utilized to encapsulate the entire assembly within a block of acrylic plastic.

When the foregoing is combined with an adult attenuator, the phantom provides an X-Ray attenuation factor comparable to that of a one hundred and eighty to one hundred and ninety pound patient. When used alone, the phantom duplicates a typical attenuation of pediatric patients up to ninety pounds.

In general use, the phantom is placed with an adult attenuator on a patient support table such as table 12. An adjustment is made as to the distance from the X-Ray focal spot to the image intensifier, namely from X-Ray tube 10 to image intensifier input phosphorous screen 26.

The distance from the top of the table 12 to the image intensifier input phosphor 26 should be approximately twelve inches.

The cine technique of the camera 24 is set for that which is routinely used for a normal sized patient.

The top of the table 12 is positioned for the phantom being in the center of the TV image. The foregoing is then such wherein the shutters are columnated to the edge of the phantom as visualized on the TV image of the TV camera 22.

A three second cine run of the phantom is then utilized in order to provide recordation on the film. The film is then processed after determining that the processing parameters are correct.

The heart, lung and diaphragm areas of the image are then measured. In particular, the heart area measured by the combination of plates 80 and those which are combined therewith in the form of the plates 60 which provide the heart image area is measured. The lung area provided by the spaces 62 is also measured and the diaphragm area provided by plate 84 in combination with all the remaining plates 80 and 60 is also then measured.

The optical density of the heart area as measured by a densitometer should be approximately 0.90 to plus or minus 0.10. The lung optical density should be 1.65 plus or minus 0.10. The optical density of the diaphragm should be 0.25 plus or minus 0.05.

As previously stated, the space 54 has the arteries 50 and 52 eliminated therefrom for allowing a densitometer to quantify the density of the optical grey characteristics of the film. This is a measurement for contrast and is utilized with the foregoing measurements.

As can be appreciated, the cardiovascular phantom of this invention provides a discrete and accurate calibration for cine cardiovascular activity. Once the setting has been established in the foregoing manner it enhances an overall user's ability to make clear and accurate cine films of a subject due to the pre-established settings of the equipment prior to a patient being filmed. As a consequence, it is believed to be a substantial step over the prior art and thereby should be accorded broad patent coverage as set forth in the following claims.

I claim:

1. A cardiovascular cine adjustment system having an X-Ray tube beneath a support table and an image intensifier with a film camera connected thereto and a TV camera for respectively viewing and recording cardiovascular activity wherein the improvement comprises:
   a cardiovacular phantom on said table between said X-Ray tube and said film camera said phantom formed from absorptive material comprising at least one layer of metallic material on a board formed in the aborescent shape of radiopaque material within the system of coronary arteries; and wherein,
   said board and absorbing material are encapsulated within a plastic material.

2. The improvement as claimed in claim 1 wherein:
   said board is a plastic board formed with said metallic material which is etched to provide said aborescent system of coronary artieries.

3. The improvement as claimed in claim 2 wherein:
   said metallic etched material comprises a lead coating.

4. The improvement as claimed in claim 3 further comprising:
   a plurality of plastic boards having said metallic etched material in the form of lead thereon placed on overlying indexed relationship to that of each other so that the appearance of said etched material conforms to an overlying series of arterial vessels of a heart.

5. The improvement as claimed in claim 4 further comprising:
   a space within said boards to provide for the absorptive characteristics of a lung field.

6. The improvement as claimed in claim 5 further comprising:
   at least one metallic plate in overlying relationship to the plurality of plastic boards to provide a heart absorptive analogous material.

7. The improvement as claimed in claim 6 wherein:
   said heart absorptive analogous material is a first copper plate.

8. The improvement as claimed in claim 7 further comprising:
   a second metallic copper plate of a lesser size indexed and overlying said plastic boards and said first copper plate for providing an analogous absorptive area to a diaphragm.

9. The improvement as claimed in claim 8 further comprising:
   a plurality of screws for holding and indexing said boards in indexed relationship with said first copper plate to provide analogous absorptive characteristics of an anatomically correct equivalent as to tissue reproduction of the coronary arteries, myocardio diaphragm and lung field; and wherein,
   said lung field is provided by a space within said first copper plate and said circuitboards.

10. A cardiovascular phantom for providing the proper indexing of a cine camera for X-Ray cineangiography comprising:
    a plastic boardlike substrate;
    a metallic X-Ray absorptive material configured with the arborescent outline of a system of coronary arteries on said plastic boardlike substrate for absorbing X-Rays; and,
    a covering material for said board.

11. The cardiovacular phantom as claimed in claim 10 wherein said board comprises:
    a circuitboard; and,
    said metallic material comprises a lead deposit thereon which has been etched to form said aborescent outline.

12. The cardiovascular phantom as claimed in claim 10 wherein:
    said board is encapsulated within a plastic material.

13. The cardiovascular phantom as claimed in claim 12 further comprising:

a plurality of circuitboards having a lead etched deposit thereon which is configured with the arborescent outline of a system of coronary arteries.

14. The cardiovascular phantom as claimed in claim 13 comprising:
a plurality of circuitboards having indexed overlying cardiovascular vessel conformations formed of said lead;
a space passing through said boards to provide for a lung field; and wherein,
said space and said boards are encapsulated within plastic.

15. The cardiovascular phantom as claimed in claim 14 further comprising:
a metallic plate having a space indexed with respect to said lung field space within said boards for providing absorptive characteristics analogous to the heart tissue.

16. The cardiovascular phantom as claimed in claim 15 further comprising:
a second plate underlying and offset from said lung field space to provide an analogous area anatomically oriented for a diaphragm.

17. The cardiovascular phantom as claimed in claim 16 wherein:
said two espective plates are formed of copper.

18. A method for adjusting cineangiographic cameras comprising:
providing a phantom having at least one board with a metallic arborescent outline of a system of coronary arteries formed of lead;
placing said phantom on a patient support table;
adjusting an X-Ray tube, said table, an image intensifier and a cine camera with respect to each other;
setting the cine program as routinely used for filming a patient;
making a cine run of the phantom;
processing the film produced during the cine run of the phantom; and,
measuring the density of at least one of the images on the film produced during the cine run.

19. The method as claimed in claim 18 further comprising:
providing a phantom wherein said board is formed of circuitboard material.

20. The method as claimed in claim 19 further comprising:
providing a phantom formed from a plurality of circuitboards with indexed overlying lead arterial vessel outlines;
providing a space within said boards forming a lung space; and,
providing at least one metallic plate for analogous representation as to X-Ray absorptive characteristics to effectuate a heart tissue area.

21. The process as claimed in claim 20 further comprising:
providing a second metallic plate to analogize the X-Ray absorptive characteristics of a diaphragm.

22. The process as claimed in claim 21 further comprising:
measuring the density of the heart, lung and diaphragm areas on the film produced during the cine run.

* * * * *